US011734988B1

(12) United States Patent
Beveridge et al.

(10) Patent No.: US 11,734,988 B1
(45) Date of Patent: *Aug. 22, 2023

(54) MEDICAL SUPPLIES DISTRIBUTION SYSTEM

(71) Applicant: UIPCO, LLC, San Antonio, TX (US)

(72) Inventors: Meredith Beveridge, Morrison, CO (US); Michael J. Maciolek, Boerne, TX (US); Robert Wiseman Simpson, Fair Oaks Ranch, TX (US); Daniel Christopher Bitsis, Jr., San Antonio, TX (US); Bobby Lawrence Mohs, San Antonio, TX (US); Manfred Amann, San Antonio, TX (US); Emily Margaret Gray, San Antonio, TX (US); Donnette Moncrief Brown, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/473,558

(22) Filed: Sep. 13, 2021

Related U.S. Application Data

(63) Continuation of application No. 16/376,267, filed on Apr. 5, 2019, now Pat. No. 11,132,860.

(60) Provisional application No. 62/753,421, filed on Oct. 31, 2018.

(51) Int. Cl.
G07F 17/00 (2006.01)
B64C 39/02 (2023.01)
G06Q 10/08 (2023.01)
G06Q 10/06 (2023.01)
G16H 40/20 (2018.01)
G06Q 20/18 (2012.01)
G06Q 10/0875 (2023.01)
G06Q 10/083 (2023.01)

(Continued)

(52) U.S. Cl.
CPC ........ *G07F 17/0092* (2013.01); *B64C 39/024* (2013.01); *G06Q 10/083* (2013.01); *G06Q 10/0875* (2013.01); *B64U 2101/60* (2023.01); *G06Q 10/06315* (2013.01); *G06Q 20/18* (2013.01); *G16H 40/20* (2018.01)

(58) Field of Classification Search
CPC .............. G07F 17/0092; B64C 39/024; B64C 2201/128; G06Q 10/0875; G06Q 10/083; G06Q 10/06315; G06Q 20/18; G16H 40/20

See application file for complete search history.

(56) References Cited

U.S. PATENT DOCUMENTS 5,012,880 A * 5/1991 Abner ..................... A61G 3/00 180/89.11
10,037,646 B2 * 7/2018 Heffron .................. G16H 10/60
11,132,860 B1 * 9/2021 Lecocke ............ G06Q 10/0875

(Continued)

*Primary Examiner* — Michael Collins
(74) *Attorney, Agent, or Firm* — Plumsea Law Group, LLC

(57) ABSTRACT

A mobile medical supplies distribution system may include a transportable chassis forming part of a motorized vehicle; a service compartment configured to house a person serving as a medical supplies distribution service agent; a supply of select medical supplies; and one or more delivery drones configured to deliver medical supplies from the service compartment to a location remote from the service compartment.

13 Claims, 7 Drawing Sheets

(51) Int. Cl.
*G06Q 10/0631* (2023.01)
*B64U 101/60* (2023.01)

(56) References Cited

U.S. PATENT DOCUMENTS

| | | | |
|---|---|---|---|
| 2002/0165641 A1* | 11/2002 | Manalang | A61G 12/001 |
| | | | 312/1 |
| 2003/0120384 A1* | 6/2003 | Haitin | A61G 12/001 |
| | | | 700/242 |
| 2006/0079994 A1* | 4/2006 | Chu | G07F 11/62 |
| | | | 700/231 |
| 2008/0303638 A1* | 12/2008 | Nguyen | G06Q 10/00 |
| | | | 707/E17.014 |
| 2015/0227127 A1* | 8/2015 | Miller | G16H 20/13 |
| | | | 700/244 |
| 2017/0032092 A1* | 2/2017 | Mink | G06Q 10/1095 |
| 2017/0079860 A1* | 3/2017 | McLoughlin | B60R 16/03 |
| 2019/0047515 A1* | 2/2019 | Ferguson | G06Q 10/0635 |
| 2019/0108900 A1* | 4/2019 | Gershfang | G06K 7/1417 |
| 2019/0278274 A1* | 9/2019 | Igata | G06Q 30/0607 |

* cited by examiner

MEDICAL SUPPLIES DISTRIBUTION SYSTEM

CROSS-REFERENCE TO RELATED APPLICATIONS

This application is a continuation of U.S. patent application Ser. No. 16/376,267, filed Apr. 5, 2019, and entitled "Medical Supplies Distribution System," which claims priority to U.S. Provisional Patent Application No. 62/753,421, filed Oct. 31, 2018, and entitled "Medical Supplies Distribution System." The entire disclosures of the above-referenced applications are incorporated herein by reference.

TECHNICAL FIELD

The present disclosure generally relates to a medical supplies distribution system and, more particularly, to a mobile medical supplies distribution system with accommodations for disaster conditions.

BACKGROUND

Following disasters, such as hurricanes, tornados, floods, etc., the businesses of a disaster locality, including pharmacies, can be left incapacitated. Some medications, such as insulin, blood pressure medication, etc., can be critical for patients. If the duration of the disaster conditions is extended or if the patient had a short supply of their medicine at the time the disaster occurred, the patient may be in need of an alternative way to obtain a new supply of their medication while their local pharmacy remains incapacitated.

There is a need in the art for a system and method that addresses the shortcomings discussed above. In particular, there is a need in the art for a medication distribution system configured to provide medication to disaster areas.

SUMMARY

The present disclosure is directed to a system and methods for distributing medication. In some embodiments, the disclosed system may include a mobile unit, such as a vehicle or trailer, which may serve as a mobile pharmacy. Also, the system may include one or more drones configured to deliver medication. In addition, in some embodiments, the disclosed system may include features to facilitate the submission of prescription information, such as uploading photos of the prescription. Further, the disclosed system may include an app or website interface to enable users to submit prescription information.

In one aspect, the present disclosure is directed to a mobile medical supplies distribution system. The system may include a transportable chassis and a service compartment configured to house a medical supplies distribution service agent. In addition, the system may include a supply of select medical supplies.

In another aspect, the present disclosure is directed to a medication distribution system. The system may include a service compartment configured to house a medication distribution service agent. In addition, the system may include a supply of select medications. Further, the system may include a communication system configured to enable real-time consultation with a medication consultant located remote from the service compartment.

In another aspect, the present disclosure is directed to a medication distribution system. The system may include a device processor. In addition, the system may include a non-transitory computer readable medium including instructions executable by the device processor to perform the following steps: submitting prescription information regarding prescription medication, received from a user of the system, to a medication distributing authority.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

The disclosed medication distribution system may include several features for providing distribution of medication in emergency situations, such as disasters, and other circumstances in which traditional pharmacies may be incapacitated. For example, in some embodiments, the medication distribution system may be mobile. For instance, the system may include a vehicle or trailer, which may serve as a mobile pharmacy. Additionally, or alternatively, an exemplary medication distribution system embodiment may include drones configured for delivering medication. In some embodiments, the disclosed medication distribution systems may be mobile as well as include medication delivery drones.

Figure 1:
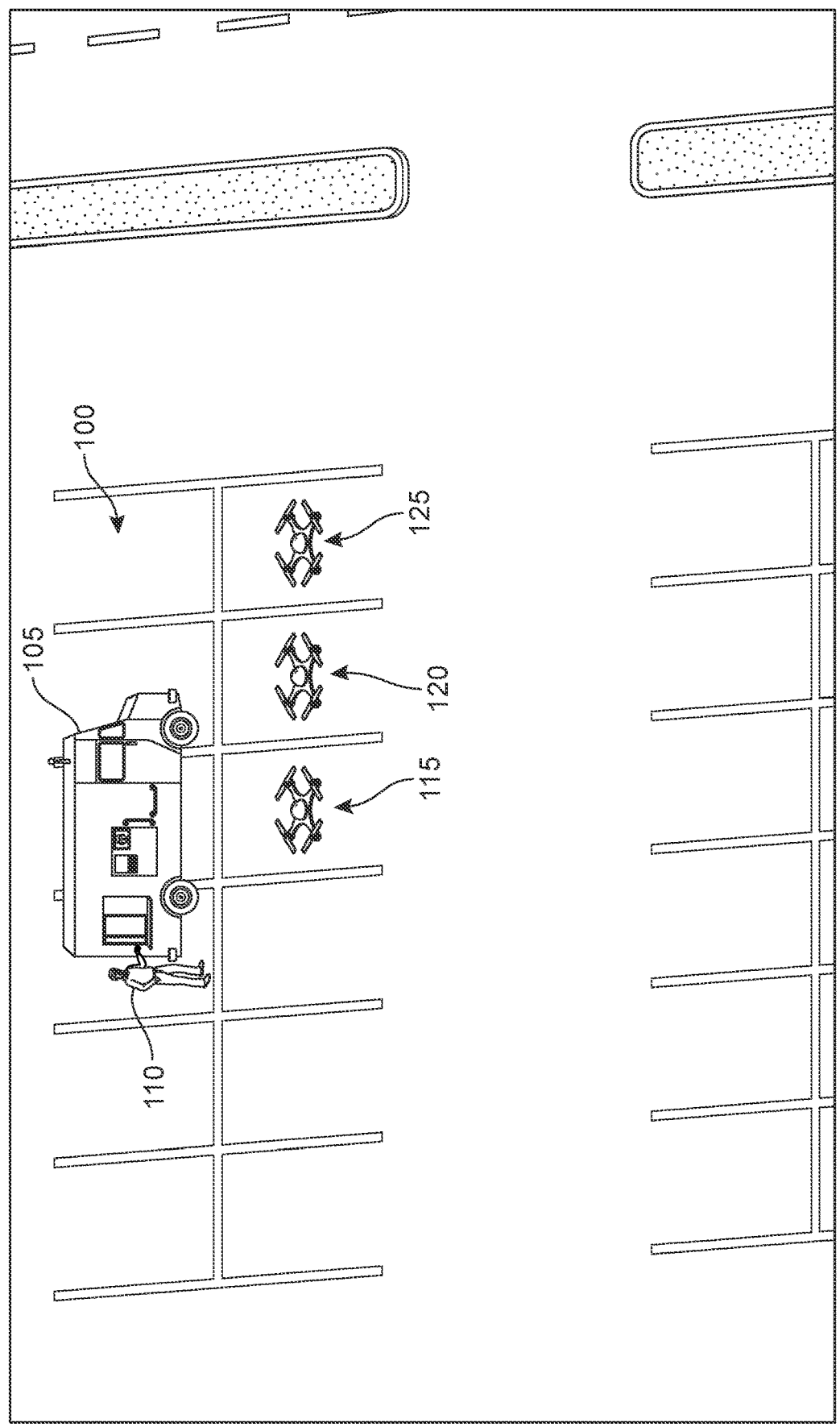
FIG. 1 is a schematic illustration of a mobile medical distribution system in a parking lot.

FIG. 1 is a schematic illustration of a mobile medication distribution system in a parking lot. As shown in FIG. 1, a medication distribution system 100 may include a medication distribution vehicle 105. FIG. 1 illustrates a user 110 visiting medication distribution vehicle 105.

The mobile pharmacy, such as medication distribution vehicle 105, may include a supply of select, common, and essential medications for distribution. Some of the medications may be over-the-counter (i.e., non-prescription), whereas other stocked medications may be prescription medications. People affected by a disaster may be in need of pain relief and/or first aid. Accordingly, the mobile pharmacy may be stocked with a supply of non-steroidal anti-inflammatory drugs (NSAIDs) and other pain relief medications, as well as first aid medications, such as antibiotic creams, sprays, etc. In addition, allergic reactions can be severe and thus require urgent treatment. Accordingly, the mobile pharmacy may be stocked with allergy medications, such as antihistamines, etc.

Some of the medications stocked in the mobile pharmacy may be commonly prescribed medications. For example, the mobile pharmacy may be stocked with insulin, high blood pressure medication, corticosteroids, and other commonly prescribed, essential medications. Exemplary essential medicines may be medications listed in the World Health Organization's List of Essential Medicines. These medicines are defined by the World Health Organization as medicines that "satisfy the priority health care needs of the population." It may not be practical to maintain a supply of all medications on the World Health Organization's List of Essential Medicines. However, this list may provide guidance as to which medications or classes of medicine should be stocked in a mobile pharmacy configured for disaster response.

In some embodiments, the system may be a medical supplies distribution system. In such embodiments, the system may be configured to distribute medical supplies including, not only medication, but other types of medical supplies. In some cases, such supplies may be provided according to prescriptions from a physician or other medical practitioner. In some embodiments, such supplies may include, for example, prescription eye glasses and/or contact lenses. In some such embodiments, the mobile pharmacy may be stocked with eye glasses and/or contact lenses in a plurality of common vision correction prescriptions. For example, eye glasses and/or contact lenses may be provided in prescriptions of predetermined intervals, in a similar way that so-called "reader" glasses are provided at brick-and-mortar pharmacy stores. For example, in some embodiments, the disclosed mobile pharmacy may be stocked with eye glasses and/or contact lenses having pre-manufactured corrective strengths, e.g., 1.0 D, 1.25 D, 1.5 D, 3.0 D, and so on, in a manner similar to available reader glasses. Further, the mobile pharmacy may be stocked with glasses and/or contact lenses that correct hyperopia (farsightedness), presbyopia (age-related farsightedness), and/or myopia (nearsightedness). In some embodiments, the mobile pharmacy may be stocked with glasses and/or contact lenses that correct astigmatism.

In some embodiments, in addition to (or instead of) medication, the mobile pharmacy may be stocked with other types of medical supplies, some of which may be distributed with a prescription. For example, in some cases, the mobile pharmacy may be stocked with medical devices, such as nebulizers, nasal spray dispensers, asthma inhalers, medical injectors, etc. In some embodiments, the mobile pharmacy may also be stocked with batteries for powering various medical devices that may be distributed by the pharmacy. Further, other types of medical supplies and equipment may be stocked in the mobile pharmacy. For example, the mobile pharmacy may be stocked with crutches, aircasts, braces, elastic bandages, first aid supplies, etc.

In some embodiments, the mobile pharmacy may be stocked with medication and/or supplies for animals, such as pets and/or livestock.

In addition, system 100 may include one or more delivery drones configured to deliver medication. For example, as shown in FIG. 1, system 100 may include a first delivery drone 115, a second delivery drone 120, and a third delivery drone 125.

The delivery drones may have any suitable configuration for carrying medication for delivery. For example, in some embodiments, the delivery drones may have a grasping device for holding a medication carrying bag or bottle. Alternatively, the drones may include one or more compartments in the body of the drone for storing a medication bag or container.

The delivery drones may have performance capabilities suitable for delivery of a variety of medications. For example, the drones may have enough power to carry heavier medications, such as liquids. In addition, the drones may have enough range, both in terms of controllability/navigation and battery life in order to deliver medications from an edge of a disaster area to locations that are centrally located within the disaster area. In some cases, the drones may be capable of delivering medication from an edge of a disaster area to an opposite edge of the disaster area. For example, if a disaster area falls along a coastline or lake, the shoreline may form the edge of the disaster area on one side. Accordingly, the closest a mobile pharmacy may be able to get to a person who is stranded along the shore could be at the opposite edge of the disaster area. Accordingly, the drones may be capable of traversing the full distance across the disaster area to complete deliveries.

In some embodiments, the drones may be autonomous. That is, the drones may be programmable to deliver to designated destinations. In other embodiments, the drones may be piloted remotely to make deliveries.

Figure 2:
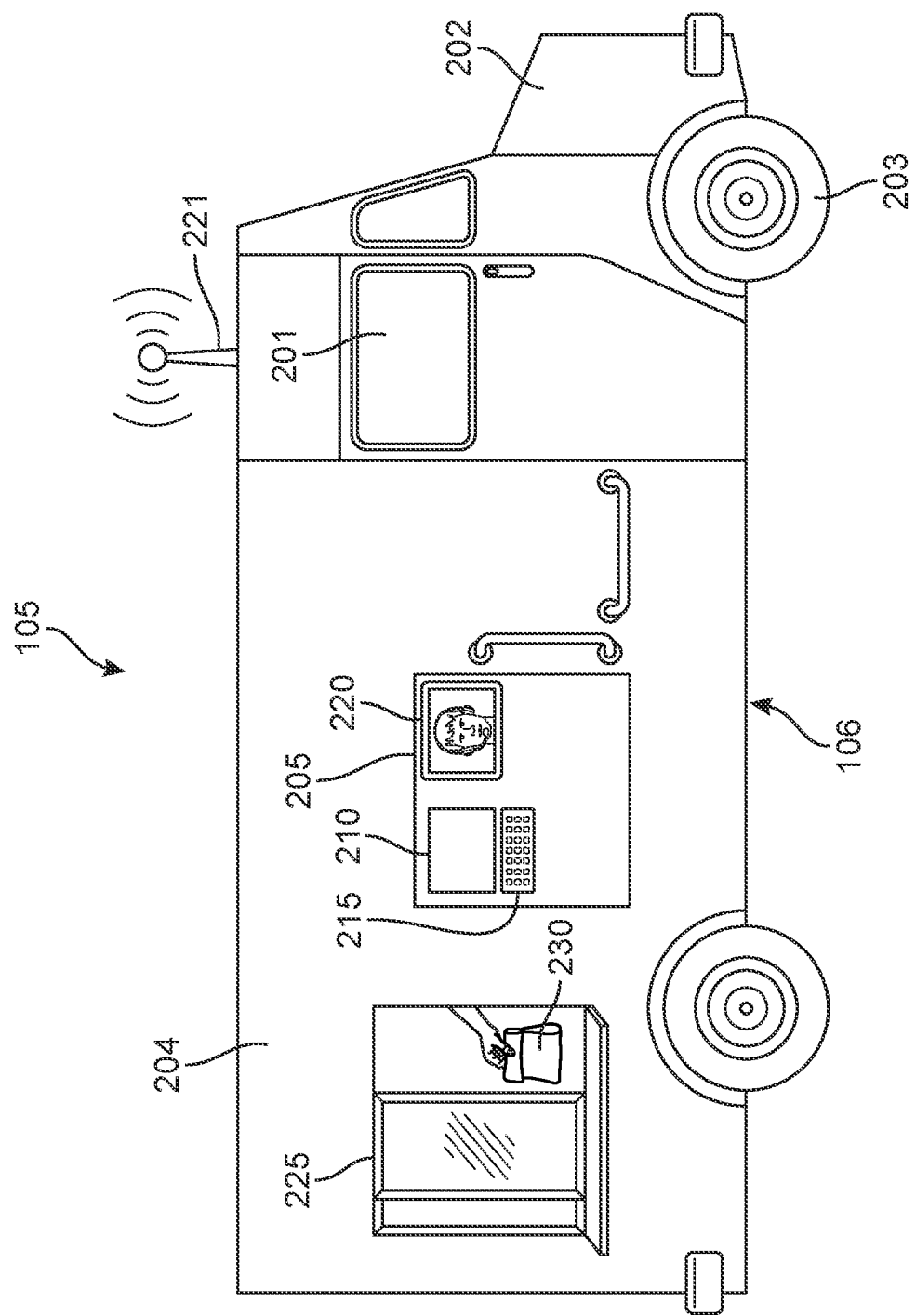
FIG. 2 is a schematic illustration of a medication distribution vehicle of the mobile medication distribution system.
Figure 3:
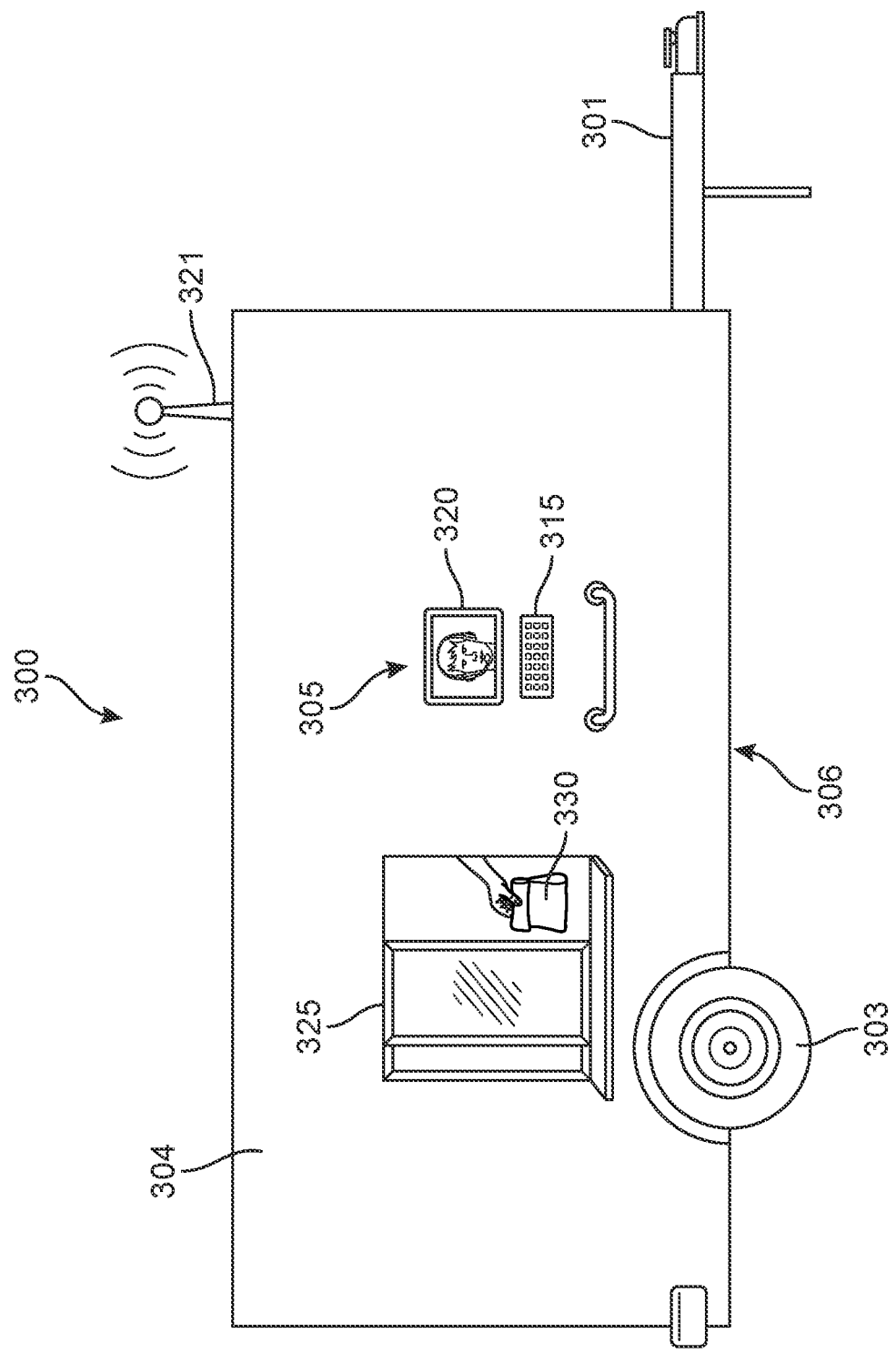
FIG. 3 is a schematic illustration of a medication distribution trailer of a mobile medication distribution system.

FIGS. 2 and 3 illustrate exemplary mobile pharmacies. In some cases, the mobile pharmacy may be configured as a vehicle, as shown in FIG. 2. Alternatively, as shown in FIG. 3, in other cases, the mobile pharmacy may be a trailer, which may be towable by a separate vehicle. The following discussion provides exemplary details of the disclosed mobile pharmacies.

A mobile pharmacy may include a transportable chassis, upon which may be mounted a service compartment. The service compartment may be configured to house a medication distribution service agent. That is, a person, such as a volunteer or disaster relief worker, may hand out medication from the service compartment. For example, the service compartment may include a delivery window through which the distribution service agent may hand medication to persons obtaining service from the mobile pharmacy.

The mobile pharmacy may also include a communication system which may facilitate communication between persons obtaining service from the mobile pharmacy and a physician or pharmacist who may be located remotely from the mobile pharmacy. Accordingly, the mobile pharmacy may service a disaster locality without requiring the in-person presence of a physician or pharmacist. An on-call physician may be predetermined to assist with disaster relief efforts by providing consultation services remotely to the mobile pharmacy. In addition, in some cases, the system may be configured for patients to communicate with their own physician or with a different pharmacy that they regularly use in a different location. For example, if a person is on vacation in an area that experiences a disaster, they may wish to contact their own physician or pharmacist before obtaining medication from a mobile pharmacy. The communication system provided on the mobile pharmacy vehicle or trailer may facilitate such communication.

The communication system may be any suitable system for communication. For example, in some embodiments, a video conference system may be provided for real-time, face-to-face communication between a physician or pharmacist and a person obtaining service from the mobile pharmacy. In other cases, an audio communication system may provide the real-time communication. Any suitable system may be utilized for video and/or audio communication. For example, a satellite, cellular, Internet, or other communication network may be utilized.

In some embodiments, the mobile pharmacy may include a transportable chassis that is part of a vehicle. For example, FIG. 2 is a schematic illustration of a medication distribution vehicle of the mobile medication distribution system. As shown in FIG. 2, vehicle 105 may include a transportable chassis 106. Vehicle 105 may include basic components of a vehicle, such as a power source 202, wheels 203, etc.

In some embodiments, power source 202 may include a combustion engine, configured to run on gasoline, diesel, ethanol, or other fuel. In other embodiments, power source 202 may include an electric motor, powered via a battery. In other embodiments, power source 202 may include a hybrid system, for example including both a combustion engine and an electric motor.

As shown in FIG. 2, vehicle 105 may include a cab 201 configured to seat one or more persons, including a driver. Cab 201 and vehicle 105 in general may have any suitable configurations. FIG. 2 illustrates vehicle 105 as a panel van or box truck. In some embodiments, other vehicle configurations may be utilized. For example, a semi truck and trailer (i.e., tractor-trailer) configuration may be utilized. This may provide a larger capacity compartment for storing medications. Not only may the extra capacity enable the mobile pharmacy to service a large number of people, but also it may enable the mobile pharmacy to store a greater variety of medications, in order to be prepared for a wide array of patient needs.

As shown in FIG. 2, vehicle 105 may include a service compartment 204 configured to house a medication distribution service agent. That is, service compartment 204 may provide a workspace within which medications may be prepared for distribution, and from which a person may distribute medication to recipients. For example, as shown in FIG. 2, vehicle 105 may include a service window 225, through which medication may be distributed by the agent. For instance, as shown in FIG. 2, medication 230 may be distributed through service window 225. Because the space within service compartment 204 may be limited and, at least partially, filled with medication storage, there may be limited space for persons. Accordingly, persons obtaining medication from vehicle 105 may do so from outside vehicle 105, e.g., through service window 225. In some embodiments, service compartment 204 may accommodate medication recipients inside, which may be beneficial in situations where harsh weather conditions persist in a disaster area.

As shown in FIG. 2, vehicle 105 may include a communication system 205 configured to enable communication with a medication consultant located remote from vehicle 105, such as a physician or pharmacist at a location remote from vehicle 105. Communication system 205 may be configured to provide an audio conference, a video conference, a text chat, or other type of communication with the remotely located consultant. In some embodiments, communication system 205 may include a display screen 220 configured to display a video of the remotely located medication consultant. Alternatively display screen 220 may display a still image of the consultant, or information (e.g., name, title, contact info, etc.) about the consultant.

Communication system 205 may also include an input display 210. Input display 210 may display an interface configured for user interaction. In some embodiments, communication system 205 may include an input device, such as a keyboard 215, as shown in FIG. 2. Other types of input devices may be used as well. For example, in some embodiments, input display 210 may be a touchscreen. In some embodiments, input display 210 may be separate from display screen 220, as shown in FIG. 2. In other embodiments, display screen 220 may serve not only as a communication display, but also as an input display.

In some embodiments, vehicle 105 may be configured to receive submission of medication information, such as prescription information. For example, in some embodiments, input display 210 may be configured to facilitate the submission of medication information. In some embodiments, vehicle 105 may include a camera with which a photograph may be taken of a patient's prescription, medication container, medication container label, and/or the medication itself (e.g., the actual pill). Using these features, a user of the system may provide medication information to the mobile pharmacy in order to obtain the desired medication.

In addition, vehicle 105 may include an antenna 221 and/or other equipment for sending and receiving communication signals. This equipment may be configured to send and receive signals including information associated with medication. For example, a patient's medical records, prescription information, etc., may be transferred from remote databases to vehicle 105 for purposes of distributing medication. In some embodiments, the systems of vehicle 105 may be configured to receive medication information, such as prescription information, from users who may submit medication requests via a personal computer or personal electronic device. For example, in some embodiments, vehicle 105 may include a prescription receiving system.

Alternatively, or additionally, the communications equipment of vehicle 105 may be configured to send and receive signals for communicating medication information to a separate location, such as a different pharmacy, for example, in instances where the mobile pharmacy may not have the requested medication in stock or in instances where a different pharmacy may be more readily accessible to the system user.

FIG. 3 is a schematic illustration of a medication distribution trailer of a mobile medication distribution system. As shown in FIG. 3, in some embodiments, the medication distribution system may include a trailer 300 towable by a vehicle. Trailer 300 may include a transportable chassis 306 and wheels 303. In addition, instead of a driver cab, trailer 300 may include a towing apparatus 301 configured for attachment to a towing vehicle. Towing apparatus 301 may have any suitable configuration. Notably, towing apparatus 301 may have any type of towing apparatus compatible with the corresponding towing apparatus of vehicles suitable for towing the trailer. For example, in some embodiments, towing apparatus 301 may be configured to be coupled to a tow hitch of a passenger vehicle, such as a pick-up truck or SUV. In other embodiments, towing apparatus 301 may be configured for coupling to a semi truck (i.e., in a tractor-trailer arrangement). Accordingly, such a towing apparatus 301 may be configured as a fifth wheel coupling.

In addition, as shown in FIG. 3, trailer 300 may include a service compartment 304 mounted on transportable chassis 306 and configured to house a medication distribution service agent. Service compartment 304 may be configured the same or similarly to service compartment 204 discussed above.

As shown in FIG. 3, service compartment 304 may provide a workspace within which medications may be prepared for distribution, and from which a person may distribute medication to recipients. For example, as shown in FIG. 3, trailer 300 may include a service window 325, through which medication may be distributed by the agent. Because the space within service compartment 304 may be limited and, at least partially, filled with medication storage, there may be limited space for persons. Accordingly, persons obtaining medication from trailer 300 may do so from outside trailer 300, e.g., through service window 325. For instance, as shown in FIG. 3, medication 330 may be distributed through service window 325. In some embodiments, service compartment 304 may accommodate medication recipients inside, which may be beneficial in situations where harsh weather conditions persist in a disaster area.

As shown in FIG. 3, trailer 300 may include a communication system 305 configured to enable communication with a medication consultant located remote from trailer 300, such as a physician or pharmacist at a location remote from trailer 300. Communication system 305 may be configured to provide an audio conference, a video conference, a text chat, or other type of communication with the remotely located consultant. In some embodiments, communication system 305 may include a display screen 320 configured to display a video of the remotely located medication consultant. Alternatively display screen 320 may display a still image of the consultant, or information (e.g., name, title, contact info, etc.) about the consultant.

Communication system 305 may also include an input device, such as a keyboard 315, as shown in FIG. 3. Other types of input devices may be used as well. For example, in some embodiments, display screen 320 may be a touchscreen.

In some embodiments, trailer 300 may be configured to receive submission of medication information, such as prescription information. For example, in some embodiments, trailer 300 may be configured to facilitate the submission of medication information. In some embodiments, trailer 300 may include a camera with which a photograph may be taken of a patient's prescription, medication container, medication container label, and/or the medication itself (e.g., the actual pill). Using these features, a user of the system may provide medication information to the mobile pharmacy in order to obtain the desired medication.

In addition, trailer 300 may include an antenna 321 and/or other equipment for sending and receiving communication signals. This equipment may be configured to send and receive signals including information associated with medication. For example, a patient's medical records, prescription information, etc., may be transferred from remote databases to trailer 300 for purposes of distributing medication. In some embodiments, the systems of trailer 300 may be configured to receive medication information, such as prescription information, from users who may submit medication requests via a personal computer or personal electronic device. For example, in some embodiments, trailer 300 may include a prescription receiving system.

Alternatively, or additionally, the communications equipment of trailer 300 may be configured to send and receive signals for communicating medication information to a separate location, such as a different pharmacy, for example, in instances where the mobile pharmacy may not have the requested medication in stock or in instances where a different pharmacy may be more readily accessible to the system user.

The systems and equipment discussed above may include computing hardware, such as a device processor, and a non-transitory computer readable medium including instructions executable by the device processor to provide the services discussed above. Further, the systems on-board the vehicle may be discrete systems, or may be networked together.

Accordingly, in some embodiments, the computer readable medium of the prescription receiving system may include instructions for receiving photos of at least one of medication container labels, medication pills, and prescription documentation. Further, the medication distribution system may include a prescription transfer system, which may be configured to transfer prescription information to a pharmacy located remote from the service compartment. And thus, the computer readable medium may include instructions for transferring prescription information to a remote location.

Figure 4:
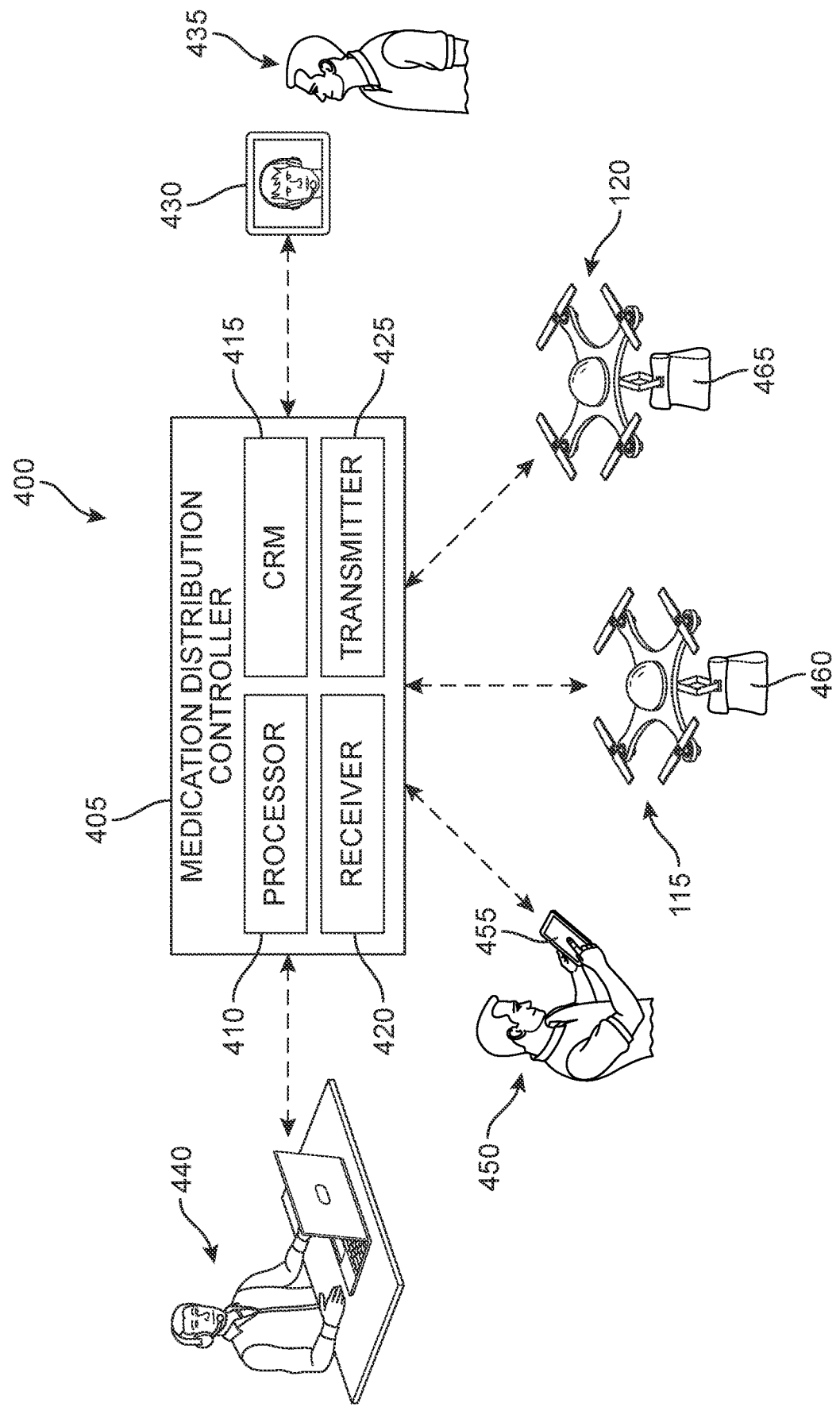
FIG. 4 is a schematic illustration of a medication distribution system network.

FIG. 4 is a schematic network illustration of a medication distribution system 400. The components of system 400 may be implemented in association with a mobile pharmacy, such as vehicle 105 and trailer 300 discussed above, or in association with a pharmacy located in a permanent building (i.e., brick and mortar establishment).

As shown in FIG. 4, system 400 may include central controller 405. Controller 405 may include various computing and communications hardware, such as servers, integrated circuits, displays, etc. Further, controller 405 may include a device processor 410 and a non-transitory computer readable medium 415 including instructions executable by device processor 410 to perform the processes discussed herein.

The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, a read-only memory (ROM), a random access memory (RAM), a static random access memory (SRAM), a portable compact disc read-only memory (CD-ROM), an erasable programmable read-only memory (EPROM or Flash memory), a digital versatile disk (DVD), a memory stick, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages, and may also include non-compiled/interpreted scripting languages such as python or JavaScript.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

Controller 405 may include networking hardware configured to interface with other nodes of a network, such as a LAN, WLAN, or other networks. In Further, controller 405 may be configured to receive data from a plurality of sources and communicate information to one or more external destinations. Accordingly, controller 405 may include a receiver 420 and a transmitter 420. (It will be appreciated that, in some embodiments, the receiver and transmitter may be combined in a transceiver.)

As shown in FIG. 4, system 400 may include a communication system 430, which enables users at a mobile pharmacy to communicate in real-time with a medication consultant, such as a physician or pharmacist. The features and capabilities of communication system 430 may be the same or similar to the communications systems discussed above with respect to FIGS. 2 and 3. Accordingly, using communications system 430, a first walkup user 435 may be able to communicate face-to-face in real-time with a medication consultant 440 who may be located remote from the mobile pharmacy. Any suitable communications platform and/or protocol may be utilized for communications between first walkup user 435 and medication consultant 440. Such platforms and protocols are discussed above in greater detail.

As shown in FIG. 4, a first remote user 450 may communicate with controller 405 using a first personal electronic device 455, such as a smart phone. Using first personal electronic device 455, first remote user 450 may submit information to controller 405. For example, first remote user 450 may submit medication information, such as prescription information, and/or medical history information, etc. The information may be delivered via Internet connection, satellite connection, telecommunications protocol, or any other platform usable by first personal electronic device 455. Because system 400 is configured to receive information electronically, first remote user 450 need not be located in proximity to a medication distribution center, such as a pharmacy, whether mobile or permanently located.

In order to distribute medication to a remotely located user, such as first remote user 450, system 400 may include one or more medication delivery drones configured to deliver medication to a location remote from a distribution center, such as a service compartment of a mobile pharmacy. For example, as shown in FIG. 4, system 400 may include first delivery drone 115, which is illustrated carrying a first medication bag 460. In order to service multiple users more efficiently, system 400 may include a plurality of drones. Accordingly, as shown in FIG. 4, system 400 may include second delivery drone 120, which is illustrated carrying a second medication bag 465. First delivery drone 115 and second delivery drone 120 may be configured to communicate with controller 405. Exemplary capabilities of first delivery drone 115 and second delivery drone 120 are discussed in greater detail above.

Any suitable communication platform and/or protocol may be utilized for communication between controller 405 and the drones. The drones may be manually controlled or autonomously controlled. In some embodiments, a global positioning system (GPS) navigation system may be utilized to facilitate the delivery of medication to remote users, such as first remote user 450. For example, in some embodiments, the user may either input a location to which they would like the medication delivered. Alternatively, controller 405 may obtain location information recorded and transmitted by the user's personal electronic device. Controller 405 may be configured to command the drones to deliver medication to the designated location or to the location otherwise retrieved from the user's device. Accordingly, computer readable medium 415 may include instructions for receiving this location information and completing the drone delivery to the received location.

In some embodiments, the platform of communication between controller 405 and first personal electronic device 455 may be the same as, or similar to, the platform of communication between controller 405 and the drones. In some embodiments, the platforms of communication may be different from one another.

Figure 5:
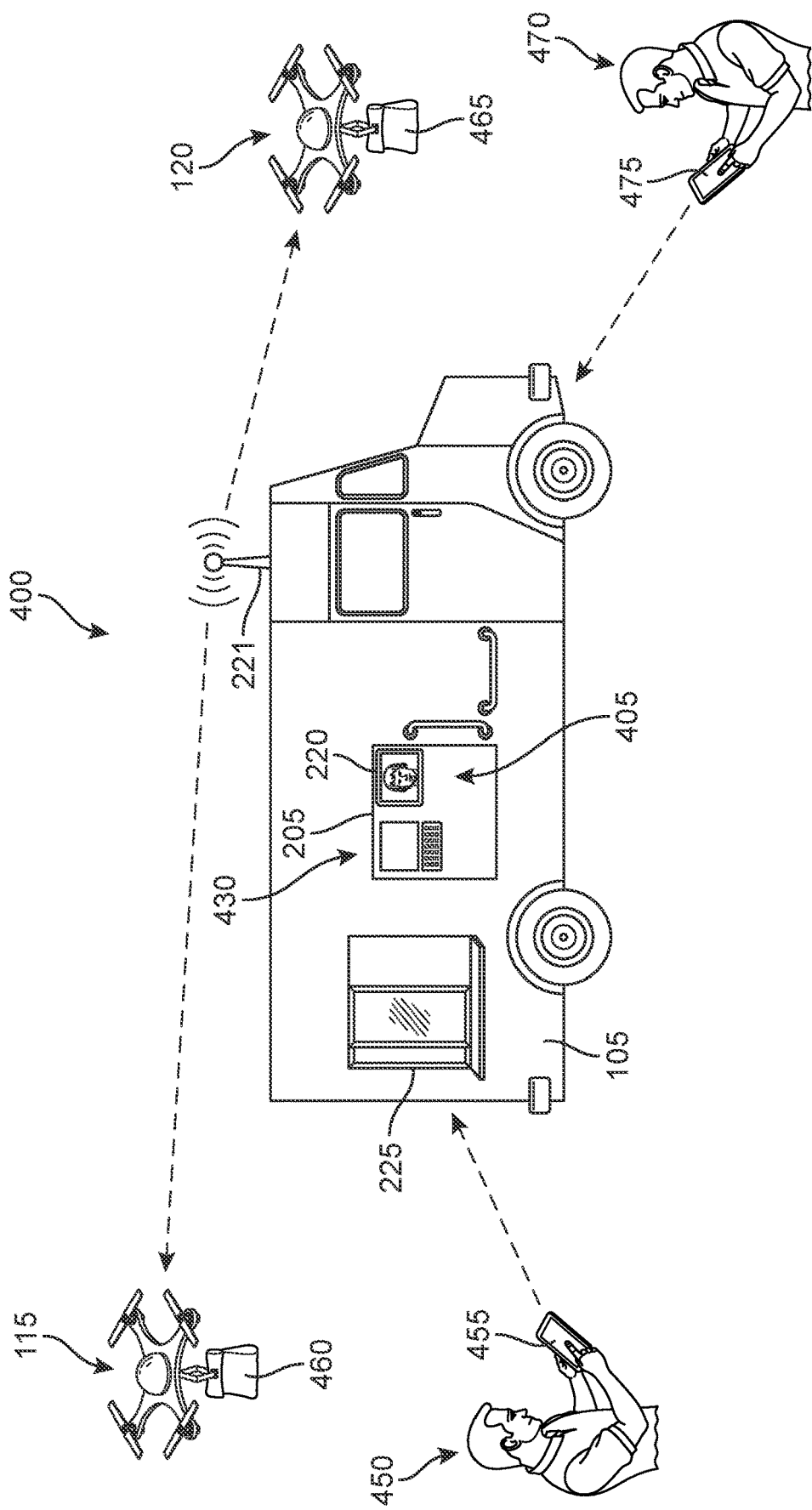
FIG. 5 is a schematic illustration of a medication distribution system with drone delivery capabilities.

FIG. 5 is a schematic illustration of a medication distribution system with drone delivery capabilities. For example, FIG. 5 illustrates medication distribution system 400 implemented with mobile pharmacy vehicle 105, first delivery drone 115 and second delivery drone 120. FIG. 5 shows multiple remotely located users submitting medication requests and delivery drones delivering the requested medication. For example, FIG. 5 shows first remote user 450 submitting a medication request using first personal electronic device 455. In addition, a second remote user 470 is shown submitting a second medication request using a second personal electronic device 475.

As shown in FIG. 5, controller 405 may be incorporated into vehicle 105. As also shown in FIG. 5, communication system 430 may be implemented as communication 205 of vehicle 105. Walkup users, such as walkup user 435 in FIG. 4, may utilize communication system 430 to communicate with a remotely located medication consultant.

Remote users, such as first remote user 450, may submit their medication request for delivery by a drone, such as first delivery drone 115, as shown in FIG. 5. Similarly, second remote user 470 may submit their medication request for delivery by a drone, such as second delivery drone 120, as shown in FIG. 5.

Figure 6:
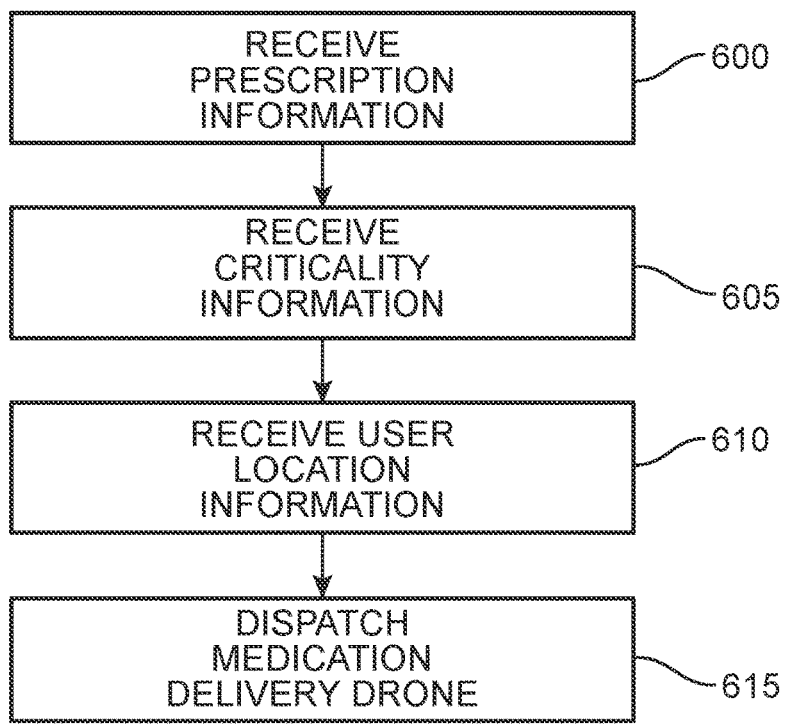
FIG. 6 is a flowchart illustrating a process of receiving prescription information from a user and dispatching a medication delivery drone to deliver the medication.

In some cases, such medication requests may be submitted as prescriptions to be filled. FIG. 6 is a flowchart illustrating a process of receiving prescription information from a user and dispatching a medication delivery drone to deliver the medication. As shown in FIG. 6, the computer readable medium of the system may include instructions for receiving prescription information (step 600). Such prescription information may be submitted in any of a variety of suitable ways. In some embodiments, the system may be configured to receive photos of prescription documentation, medication labels, medication containers, or the pills themselves.

In addition, the computer readable medium of the system may include instructions for receiving criticality information (step 605). Such criticality information may be any information that provides an indication as to how critical and/or urgent it is for the patient to receive the requested medication. Such information may include patient information, such as age, condition, risk assessment, other medical conditions, remaining dosages of existing prescription, etc. Such information may enable the system to prioritize medication deliveries to those having the most urgent need, such as the elderly, infants, and gravely ill.

Also, the computer readable medium of the system may include instructions for receiving user location information (step 610). In some cases, the user may submit a location at which they would like the medication delivered. In other cases, information from the location services on the user's personal electronic device may be received by the system to determine where to deliver the requested medication. Further, the computer readable medium of the system may include instructions for dispatching a delivery drone (step 615) once the various pieces of information discussed above have been received and processed.

In some cases, the system may include a prescription transfer system be configured to transfer prescription information to a pharmacy located remote from the service compartment of a mobile pharmacy. For example, if the mobile pharmacy, which may have a limited supply of medications both in terms of amount and variety, does not have the requested medication in stock, the medication distribution system of which the mobile pharmacy is a part may transfer the request for medication to a different medication distribution center, such as a different pharmacy.

Figure 7:
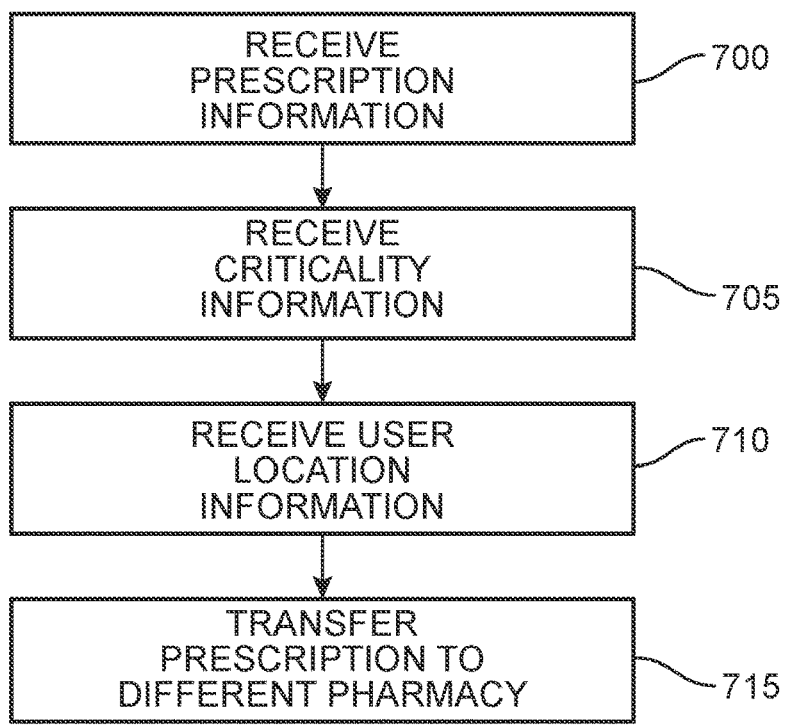
FIG. 7 is a flowchart illustrating a process of receiving prescription information from a user and transferring the prescription information to a different pharmacy.

FIG. 7 is a flowchart illustrating a process of receiving prescription information from a user and transferring the prescription information to a different pharmacy. As shown in FIG. 7, the computer readable medium of the system may include instructions for receiving prescription information from a user (step 700). For example, the system may include instructions for receiving uploaded photos of at least one of medication container labels, medication pills, and prescription documentation.

In addition, the computer readable medium of the system may include instructions for receiving criticality information (step 705). As noted above, criticality information may enable the system to prioritize medication deliveries to those having the most urgent need, such as the elderly, infants, and gravely ill. For example, if a medication request has a low criticality, the medication distribution system including a mobile pharmacy may suggest that the user simply wait to fill the prescription until they can access a permanent pharmacy. Alternatively, if a medication request has a high criticality, the system may transfer the request to a different medication distribution center (step 715).

Figure 8:
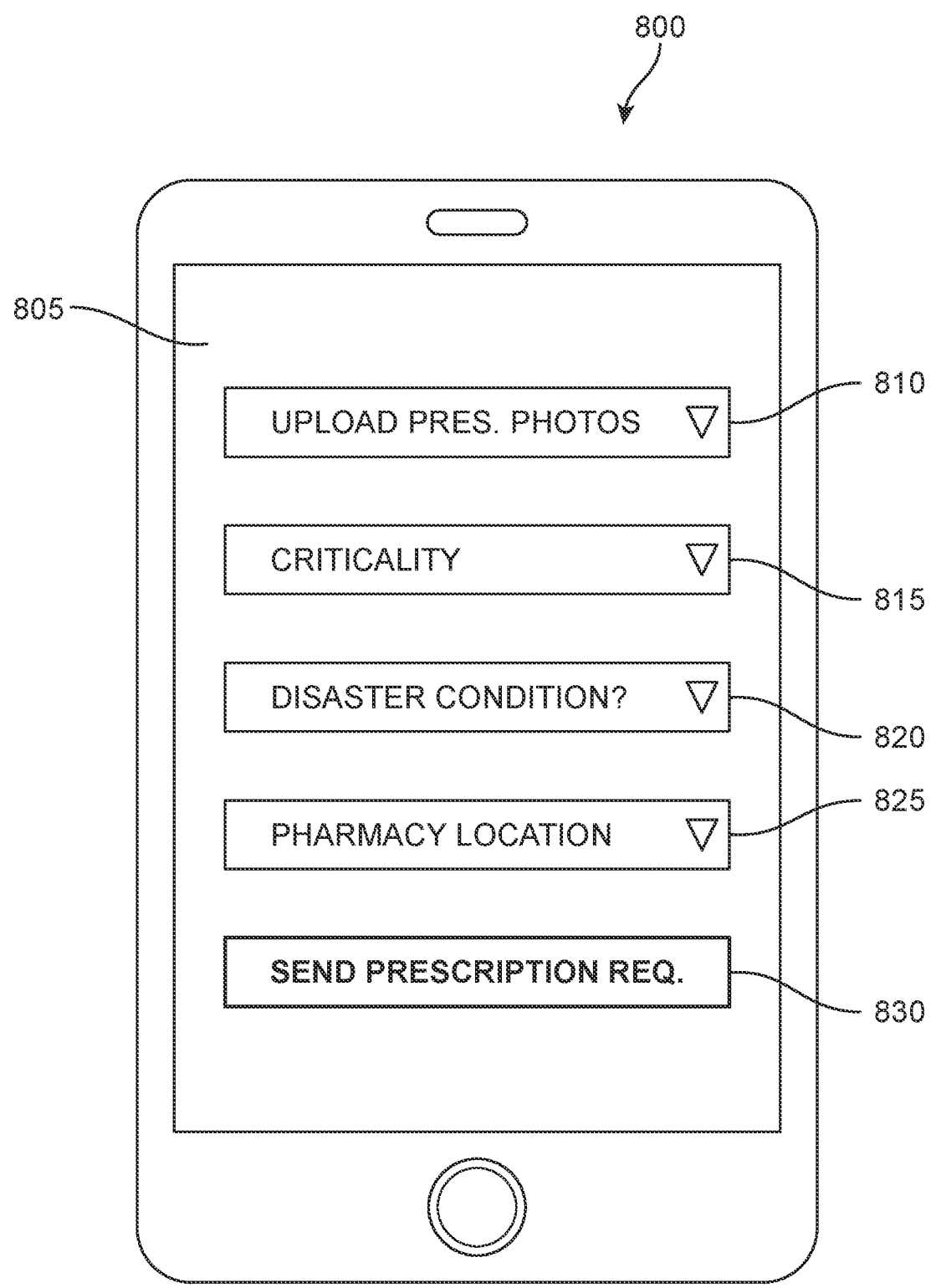
FIG. 8 is a schematic illustration of a personal electronic device displaying a user app of a medication distribution system.

In order to facilitate submission of medication information, such as prescription information, a web-based interface or mobile device app may be provided. FIG. 8 is a schematic illustration of a personal electronic device 800 displaying a user app of a medication distribution system. As shown in FIG. 8, personal electronic device 800 may include a graphical user interface 805.

Personal electronic device 800 may include a device processor and a non-transitory computer readable medium including instructions executable by the device processor. For example, the computer readable medium may include instructions for submitting prescription information regarding prescription medication, received from a user of the system, to a medication distributing authority. For example, the computer readable medium of the system may include instructions for receiving (e.g., uploading) photos of at least one of medication container labels, medication pills, and prescription documentation (step 810).

In addition, the computer readable medium of the system may include instructions for submitting information regarding the criticality of a medication to the person for whom the medication is prescribed (step 815). As discussed above, such criticality information may be any information that provides an indication as to how critical and/or urgent it is for the patient to receive the requested medication.

In addition, the computer readable medium of the system includes instructions for submitting information regarding whether the person for whom the medication is prescribed is located where a disaster condition exists (step 825). This information may include an identification of the type of disaster and the conditions in the aftermath. For example, the user may be able to choose from a predetermined list of disasters, such as hurricanes, floods, tornados, etc. In addition, the user may be able to select from a predetermined list of conditions, such as power outage, flooded home, home destroyed, water contaminated, etc. This information may indicate the possible duration of time before which the user may have access to a regular pharmacy. This information may also enable the system to prioritize incoming medication requests.

In some cases, users may wish to pick up the medication at a medication distribution center of their choosing. Accordingly, in some embodiments, the computer readable medium of the system may include instructions for identifying pharmacy locations in proximity to the system user (step 825). In the app, the user may be able to select from a list of nearby pharmacies, including mobile and/or permanent pharmacies at which to have their prescription prepared for pick up. Accordingly, in some embodiments, the computer readable medium of the system may include instructions for identifying current locations of one or more mobile pharmacies. The identification of nearby pharmacies may include a map and/or address information for the available pharmacies. Further, the computer readable medium of the system may include instructions for selecting a pharmacy location to which to send a request to fill a prescription.

In addition, the computer readable medium of the system may include instructions for sending a prescription request to a select medication distribution center (step 830), such as a mobile pharmacy, permanent pharmacy, physician's office, or other medication distribution outlet.

The embodiments discussed herein may make use of methods and systems in artificial intelligence to improve efficiency and effectiveness of the disclosed systems. As used herein, "artificial intelligence" may include any known methods in machine learning and related fields. As examples, artificial intelligence may include systems and methods used in deep learning and machine vision.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

We claim:

1. A mobile medical supplies distribution system, comprising:
   a transportable chassis forming part of a motorized vehicle;
   a service compartment configured to house a person serving as a medical supplies distribution service agent;
   a supply of select medical supplies; and
   one or more delivery drones configured to deliver medical supplies from the service compartment to a location remote from the service compartment.

2. The system of claim 1, wherein the medical supplies include medications or medical devices.

3. The system of claim 1, wherein the medical supplies include at least one of the following:
   prescription eye glasses or contact lenses;
   medical equipment; and
   first aid supplies.

4. The system of claim 1, further including a prescription receiving system including: a device processor; a camera; and a non-transitory computer readable medium including instructions, executable by the device processor, for receiving prescription information from photos of at least one of medication container labels, medication pills, and prescription documentation.

5. The system of claim 4, further including a prescription transfer system configured to transfer prescription information to a pharmacy located remote from the service compartment.

6. The system of claim 1, wherein the computer readable medium of the system includes instructions for submitting information regarding whether the person for whom the medication is prescribed is located where a disaster condition exists.

7. The system of claim 1, wherein the computer readable medium of the system includes instructions for identifying pharmacy locations in proximity to the system user.

8. The system of claim 7, wherein the computer readable medium of the system includes instructions for identifying current locations of one or more mobile pharmacies.

9. A medication distribution system, comprising:
   a transportable chassis forming part of a trailer towable by a motorized vehicle;
   the chassis including a service compartment configured to house a person serving as a medication distribution service agent;
   a supply of select medications;
   a communication system configured to enable real-time consultation with a medication consultant located remote from the service compartment;
   wherein the communication system includes a user interface disposed on an exterior of the transportable chassis; and
   one or more delivery drones configured to deliver medication from the service compartment to a location remote from the service compartment.

10. The system of claim 9, further including a prescription transfer system configured to transfer prescription information to a pharmacy located remote from the service compartment.

11. The system of claim 9, wherein the system includes a prescription receiving system configured to receive prescriptions.

12. The system of claim 11, wherein the prescription receiving system is configured for receiving photos of at least one of medication container labels, medication pills, and prescription documentation.

13. The system of claim 9, wherein the computer readable medium of the system includes instructions for submitting information regarding whether the person for whom the medication is prescribed is located where a disaster condition exists.

* * * * *